United States Patent [19]

Luber et al.

[11] Patent Number: 5,667,186

[45] Date of Patent: Sep. 16, 1997

[54] STAND FOR MOUNTING VARIOUS LOADS

[75] Inventors: Joachim Luber, Essingen-Forst; Martin Pelzer, Heidenheim; Heinz Jakubowski, Oberkochen; Arvids Mackevics, Unterkochen; Annette Reiss, Heidenheim; Jürgen Schweizer, Westerhofen, all of Germany

[73] Assignee: Carl-Zeiss-Stiftung, Heidenheim, Germany

[21] Appl. No.: 263,355

[22] Filed: Jun. 21, 1994

[30] Foreign Application Priority Data

Jun. 21, 1993 [DE] Germany .................. 43 20 443.0
Oct. 6, 1993 [DE] Germany .................. 43 34 069.5

[51] Int. Cl.$^6$ .................................................. F16M 13/00
[52] U.S. Cl. .............. 248/550; 248/297.11; 248/123.11; 248/648; 901/48
[58] Field of Search ........................... 248/550, 188, 248/183, 281.1, 297.1, 280.4, 123.1, 648; 414/917, 719; 901/48

[56] References Cited

U.S. PATENT DOCUMENTS

| | | | |
|---|---|---|---|
| 4,229,136 | 10/1980 | Panissidi | 414/719 |
| 4,339,100 | 7/1982 | Heller et al. | 248/123.1 |
| 4,548,374 | 10/1985 | Thompson | 248/123.11 |
| 4,659,278 | 4/1987 | Doege | 414/917 |
| 4,741,607 | 5/1988 | Heller | 248/123.1 |
| 5,205,522 | 4/1993 | Nakamura | 248/123.1 |
| 5,213,293 | 5/1993 | Muentener et al. | 248/281.1 |
| 5,257,998 | 11/1993 | Ota | 414/917 |
| 5,288,043 | 2/1994 | Tigliev | 248/123.1 |
| 5,332,181 | 7/1994 | Schweizer et al. | 248/648 |
| 5,397,323 | 3/1995 | Taylor | 901/48 |
| 5,456,130 | 10/1995 | Pierson | 414/719 |

Primary Examiner—Leslie A. Braun
Assistant Examiner—Gwendolyn W. Baxter
Attorney, Agent, or Firm—Walter Ottesen

[57] ABSTRACT

A stand is provided for mounting various loads and is balanced at least partially automatically. The stand includes a plurality of interconnected elements defining one or more axes about which the stand is movable. An open-loop or closed-loop control circuit is provided for at least one of the axes and detects the unbalanced state about the one axis. The control circuit allows a torque compensating device to operate on the one axis until a state of equilibrium is obtained.

32 Claims, 9 Drawing Sheets

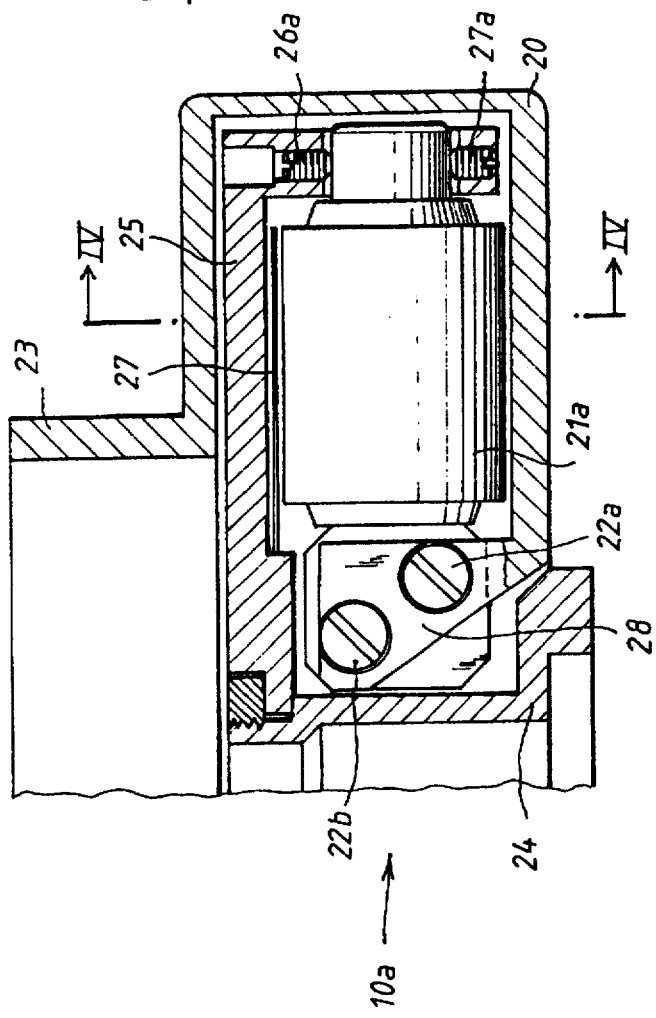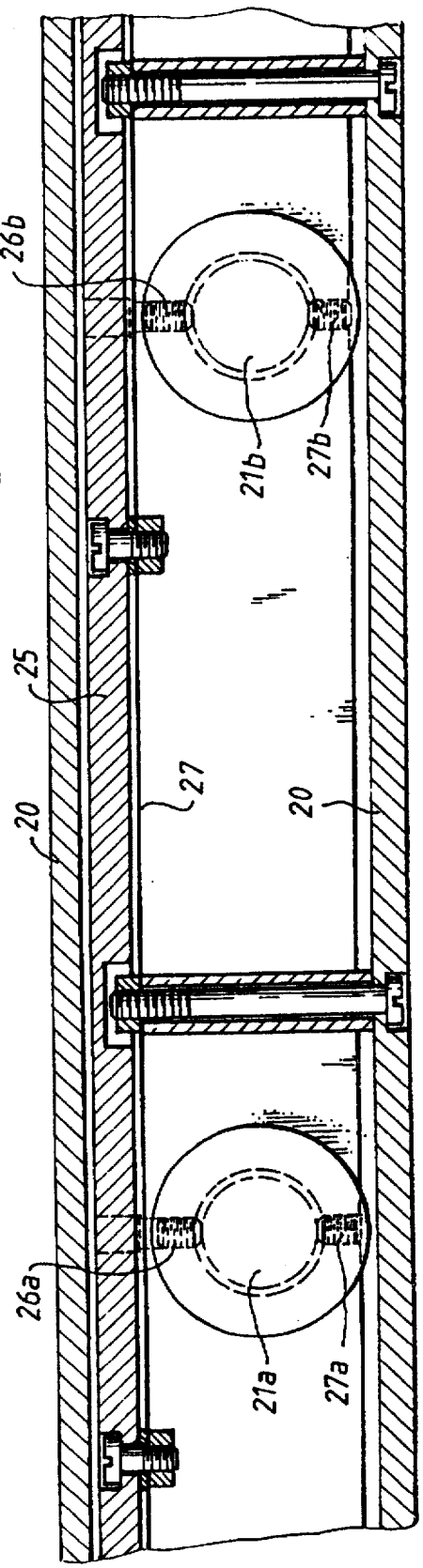

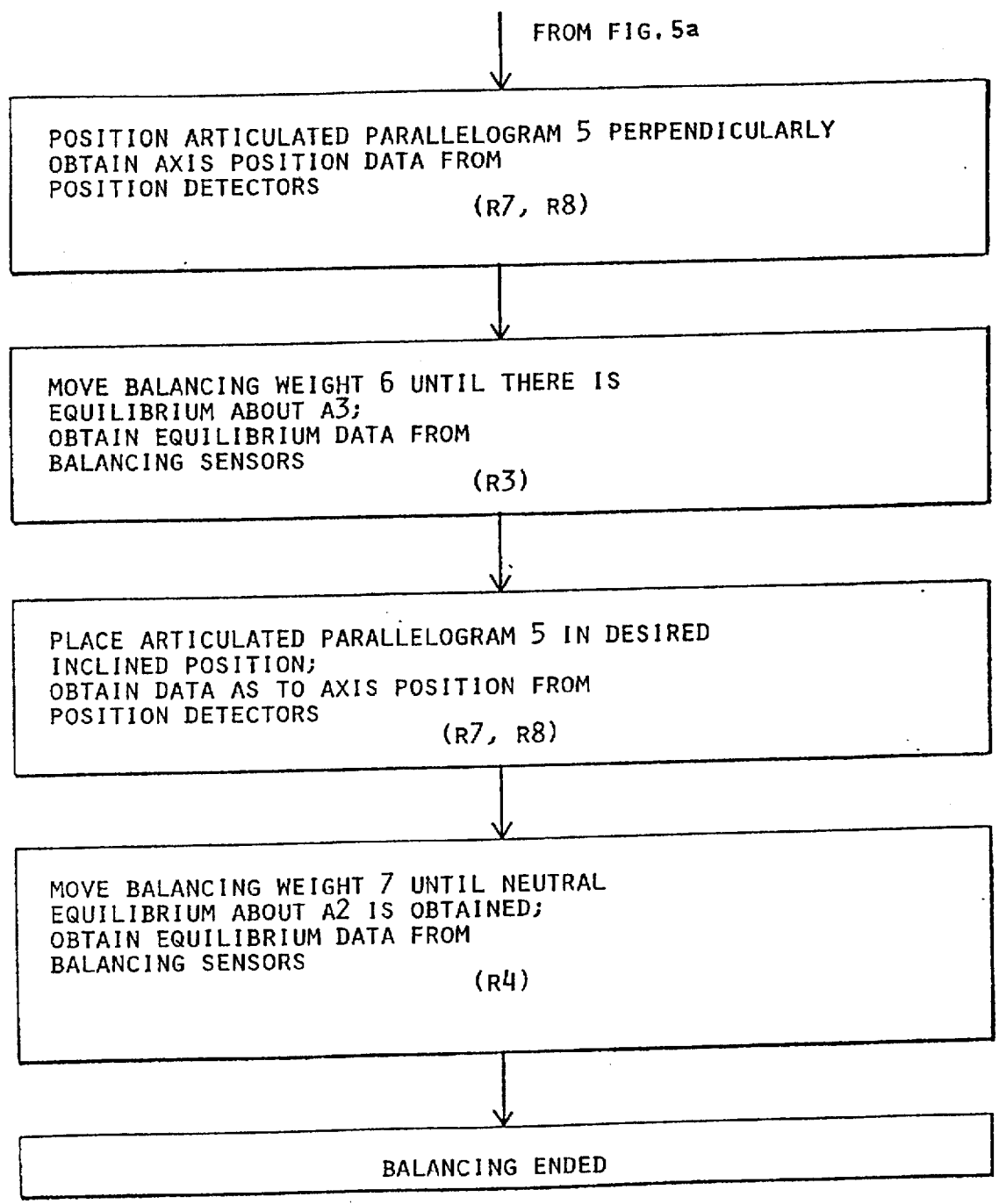

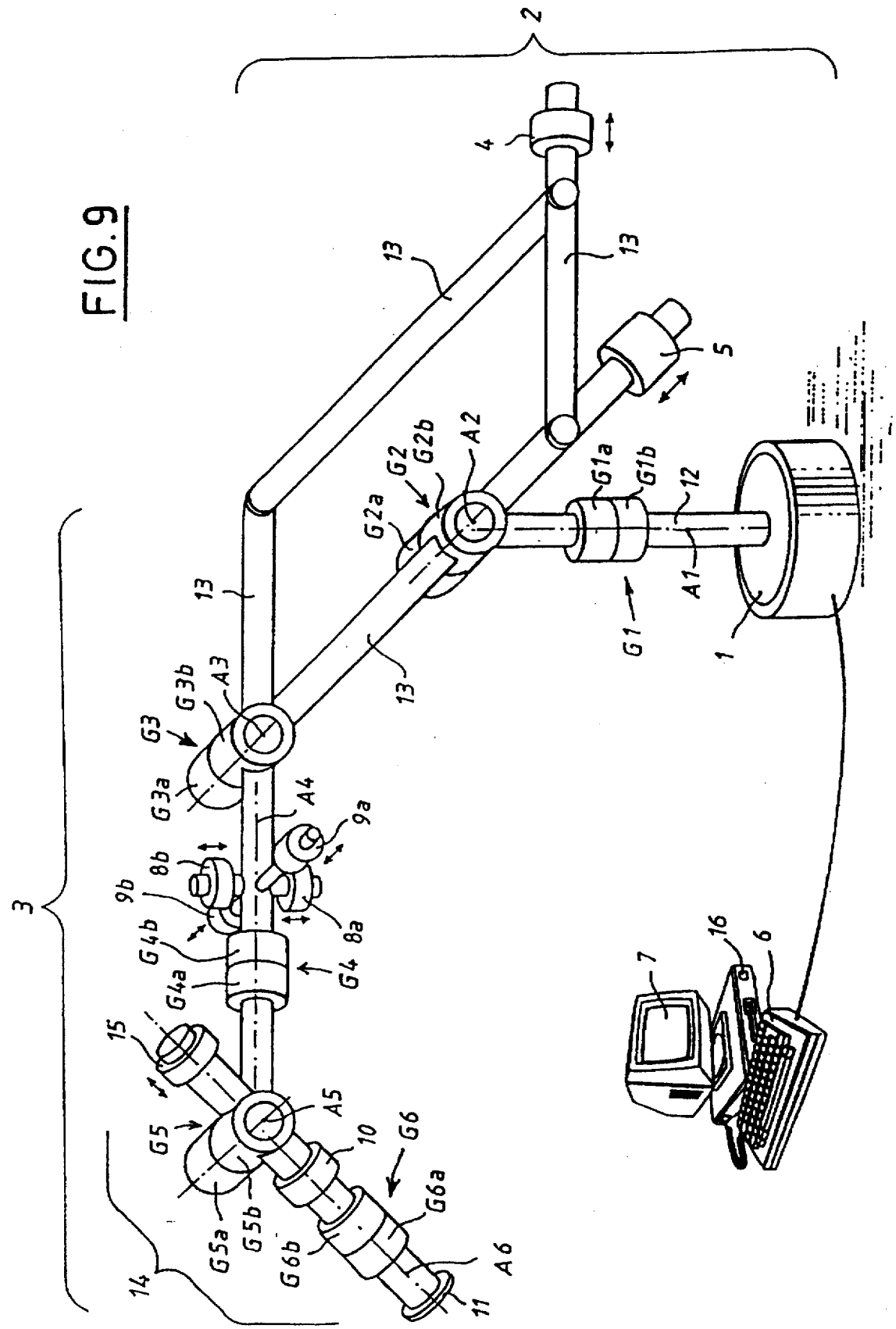

STAND FOR MOUNTING VARIOUS LOADS

FIELD OF THE INVENTION

The invention relates to a stand for arranging various loads. Balancing of the stand is at least partially automated and the stand is movable about one or more axes. The invention also relates to a suitable method for balancing the stand in an at least partially automated manner.

BACKGROUND OF THE INVENTION

Stands utilized in medicine and especially for neurosurgery are usually balanced before they are actually used. Such balancing is as a rule required in order to compensate for the forces which are caused by the loads, such as a surgical microscope, arranged on the stand. These forces are compensated so that an approximately force-free guidance of the stand and the load mounted thereon is possible for the particular operator. After being balanced, the entire stand including the load arranged thereon can stay in place in each possible practical position. Balancing is achieved by a manual or electric motorized displacement of counterweights or by pretensioning springs in order to produce a neutral state of equilibrium corresponding to the particular load on the stand.

A stand wherein such balancing before actual use is achieved manually, is, for example, disclosed in U.S. Pat. No. 4,339,100.

Manual balancing by the user is performed by moving the individual axes of the stand one after the other by hand in a prescribed sequence into specific positions. For this purpose, the user releases the corresponding electromagnetic brakes of the axis in order to release that particular axis. The user draws a conclusion as to the actual balanced or unbalanced state by observing the behavior of the axis. In this connection, a return movement of the axis can show that a stable equilibrium is present. A further tilting of the axis indicates that an unsteady equilibrium is present. However, an equilibrium state is desired wherein the gravity center of the axes or of the system of axes plus the applied loads producing torque lies at the pivot point of the axis or on a defined straight line through the pivot point of the axis. The first case is identified in the following as a neutral equilibrium state. The load application points and/or points where balancing forces are applied must be moved with respect to the axis to be balanced in dependence upon which state is present and which axis should be balanced. This is repeated until the axis no longer moves after a displacement. If this is the case, then the total gravity center of all masses, which apply a torque to an axis, lies in the particular axis or, alternately, on a defined straight line through the pivot point of the axes.

The manual balancing procedure is relatively complex to carry out, time consuming and is burdened with certain inaccuracies.

SUMMARY OF THE INVENTION

It is an object of the invention to at least partially automate the manual balancing procedure and to provide a suitable arrangement for this purpose. A simplification of the balancing of the stand is to be achieved for the particular user. It is also an object of the invention to reduce the number of positions into which the stand must be brought. Also, an increased precision in balancing is sought.

The stand of the invention to be balanced can now be balanced before use with reduced effort. This provides a shorter preparatory time before the actual operation. In addition, and because of the automated balancing procedure, an increased precision with respect to the desired neutral equilibrium state of each axis is realized which is greater than was the case with a simple estimation of the adjusted equilibrium state.

The stand to be balanced according to the invention can be partially or even completely automatically balanced depending upon the desired configuration. Thus, a separate balancing of only one axis is possible by utilizing the X-Y displacing device which is a feature of the invention; whereas, other axes can still be manually equilibrium as known per se.

Optional control loops are provided for balancing which cause torque compensating means to act on one or more axes until the desired equilibrium state of the particular axis is reached.

Additional control loops are provided for a completely automatically balanced stand and these loops provide a defined positioning about the individual axes.

In an alternate embodiment of the stand of the invention, the nonequilibrium state of the unbalanced stand is not detected via force or torque sensors; instead, the rotational movements about the individual axes resulting from the unbalanced state are detected by angle encoders which act as balancing sensors. Traversed distances are detected for each axis within a defined time duration. From these traversed distances, torque compensating means are acted upon via an iterative procedure until the entire stand is in equilibrium.

This embodiment of the invention permits partially or complete automatic balancing of the stand. In addition, this embodiment permits a stand of this kind to be utilized stereotactically. The angle encoders utilized as equilibrium sensors, can be applied for determining stereotactical coordinates during operations.

BRIEF DESCRIPTION OF THE DRAWINGS

The invention will now be described with reference to the drawings wherein:

FIG. 3 is a section view through the sensor assembly of the X-Y displacing device incorporating a force sensor mounted therein;

FIG. 4 is a developed view of the sensor assembly of FIG. 3;

FIGS. 5a and 5b show a flowchart for the automated sequence of the balancing of the complete stand in accordance with the closed-loop control principle;

DESCRIPTION OF THE PREFERRED EMBODIMENTS OF THE INVENTION

Figure 1:
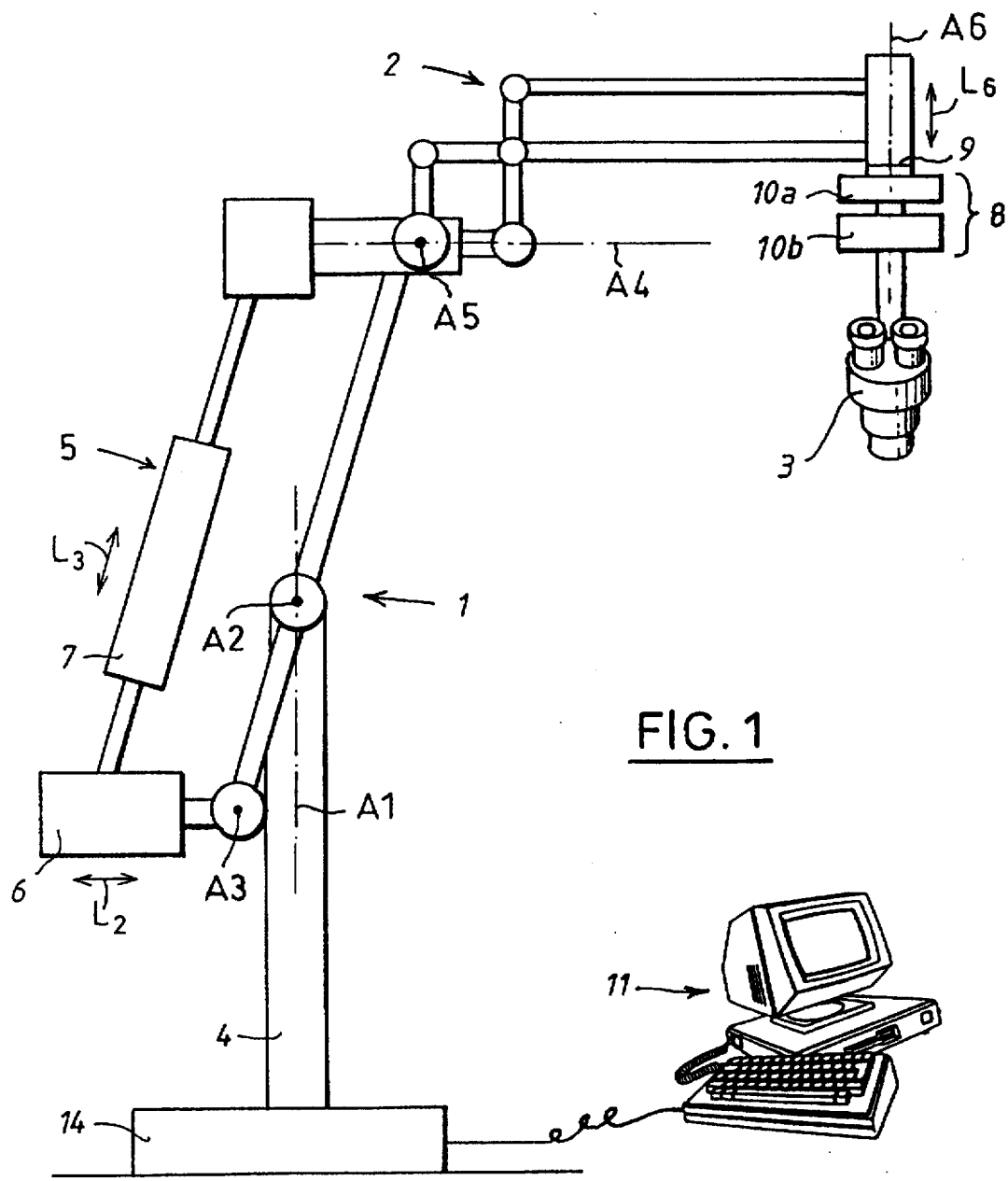
FIG. 1 is a schematic representation of a first embodiment of the stand of the invention shown including the orientation of the axes to be balanced.

FIG. 1 is a schematic representation of a first embodiment of the stand according to the invention which can be balanced. This medical stand is utilized especially in neurosurgery and the basic configuration thereof is already disclosed in U.S. Pat. No. 4,339,100 incorporated herein by reference. As mentioned above, balancing of the stand disclosed in this patent is performed in several individual manual steps.

The stand which can be balanced comprises a vertical column 1 on which a carrier arm 2 is articulately mounted. The carrier arm 2 is aligned essentially horizontally and a load in the form of a surgical microscope 3 is suspended at an interface 9 of the arm. In addition to the surgical microscope 3 shown or in lieu thereof, various additional loads such as videocameras, et cetera can be mounted on the interface 9 of the carrier arm 2.

The various carrier arm axes (A4, A5, A6) are balanced by displacing the particular load along the axis A6 when at least partially automatically balancing the stand of the invention. Thereafter, balancing of the column axes (A2, A3) is performed by displacing the balancing weights (6, 7).

In the embodiment shown in FIG. 1, the vertical column 1 of the stand comprises a base assembly (4, 14) which includes an upper base part 4 and a lower base part 14. The vertical column 1 further includes an articulated parallelogram 5 mounted so as to be movable about the horizontal axis A2 with respect to the upper part 4 of the base assembly (4, 14). The vertical upper part 4 is, in turn, movable about a vertical axis A1 relative to the lower part 14 of the base assembly (4, 14). The articulated parallelogram 5 includes the two balancing weights (6, 7) which are motor-displaceable on threads in the direction of arrows $L_2$ and $L_3$, respectively. The actual positions of the balancing weights on the articulated parallelogram 5 are detected by means of position detectors (not shown). As suitable position detectors, known inductive displacement sensors, potentiometric displacement sensors or even incremental displacement sensors or absolute-coded displacement sensors can be used and can be obtained in a large selection from the Heidenhain Company of Germany.

The articulated parallelogram 5 is further movable in itself about the horizontally-orientated axis A3.

A double articulated parallelogram is articulately mounted at the upper end of the articulated parallelogram 5. The double articulated parallelogram is in the form of a horizontal carrier arm 2 and is movable about the axis A4 and A5 relative to the articulated parallelogram 5 of the vertical column 1. The axis A5 is orientated in the same manner as the axes A2 and A3, that is, the axis A5 is aligned horizontally. The axis A4 is orientated perpendicularly to the axis A5.

The particular load and the X-Y displacing device 8 mounted between the interface 9 and the particular load are attached to the other end of the horizontal carrier 2 at the interface 9. The load together with the X-Y displacing device 8 can be displaced by motor means along the axis A6. The X-Y displacing device 8 is configured in two parts in the embodiment shown. A first part is a motorized positioning unit 10b which provides a defined displacement in one plane. This is the X-Y plane when the axis A6 is perpendicularly aligned and when Z identifies the vertical coordinate direction. The other part of the X-Y displacing device 8 is identified in the following as a sensor unit 10a and includes at least one balancing sensor which detects the load forces applied to the X-Y displacing device 8 or detects the torque acting on the axis A6 when the gravity center does not lie in the extension of the axis A6. The detail assembly of the X-Y displacing device 8 is explained below in detail with respect to FIGS. 2 to 4.

The stand also includes electromagnetic brakes (not shown) for each axis as they are known also for stands which are balanced manually. The individual axes can be selectively fixed or released in a defined manner by means of these electromagnetic brakes.

A control unit 11 having a computer is provided for the stand of the invention. The open-loop control or closed-loop control for individual axes to be balanced is realized in the computer by software. The user can start or modify the automated balancing procedure via an operating console.

In the first embodiment shown, each axis (A2 to A6) to be balanced is assigned at least one balancing sensor which detects a possible unbalanced state relative to the particular axis; that is, the closed-loop control variation of the stand which can be balanced automatically is shown. The open-loop variation does not need balancing sensors of this kind for each axis to be balanced. Drives for the motorized displacement of the axes A1 to A6 are provided for the stand which can be completely automatically balanced. Suitable servomotors operate as drives and can be driven via corresponding control loops of the control unit. These control loops further include position detectors, which can detect the particular axis position, such as suitable angle encoders.

The vertical axis A1 is usually balanced when the lower part 14 of the base assembly rests on a level surface; that is, no separate balancing is required as a rule for this axis. A control with respect to the lower part 14 is possible via a spirit level or the like which is integrated into the lower part 14 of the base assembly.

A neutral equilibrium state is sought for each of the axes A2, A4 and A6 of the stand. This is the case when the gravity center of all masses, which apply a torque to the particular axis, lie in the particular pivot point, that is, when the applying torques of this axis compensate each other. For this purpose, torque compensating means act on the particular axis to be balanced until the neutral equilibrium state is reached. At the same time, the actual unbalanced state is detected by means of the balancing sensors.

An equilibrium state is sought for the axes A3 and A5 which is obtained when the gravity point of all masses, which apply a torque to the particular axis, lies on a straight line on the extension of the axis pivot point. This equilibrium state is achieved in the same manner as the neutral equilibrium state described initially herein.

The automated balancing of the stand of the invention can be realized either in accordance with the principle of a closed-loop control or in accordance with the principle of an open-loop control. The particular flowcharts including the individual method steps with respect to the corresponding balancing procedures are explained below. It is in no way required that the entire stand be balanced in such a manner; instead, and in dependence upon the desired configuration of the stand, only an automatic balancing of one axis can take place, for example, while the other axes are balanced manually.

Force sensors which detect static forces can be used as possible balancing sensors which detect the particular unbalanced state of an axis. Accordingly, it is, for example, possible to block axial movements by means of latching bolts and the forces acting on the latching bolts can be detected with force sensors. Furthermore, balancing sensors can be utilized which detect relative inclinations of the axes. Likewise, the use of torque sensors is possible which are mounted free of torque on the particular axis and which detect the torque acting on the particular axis directly.

Motor-displaceable balancing weights as shown in the first embodiment can be utilized as torque compensating means for each axis. Alternately, the defined adjustment of compensating torques by motor-displaceable springs is also possible. The actual positions of the motor-displaceable balancing weights are detected by means of known position detectors. This applies likewise for the particular actual state of compression of the springs which is detected by position detectors.

As an example of an individual automated balancing procedure, the balancing of the axis A6 as well as the X-Y displacing device 8 required therefor is described in the following with respect to FIGS. 2 to 4.

Figure 2:
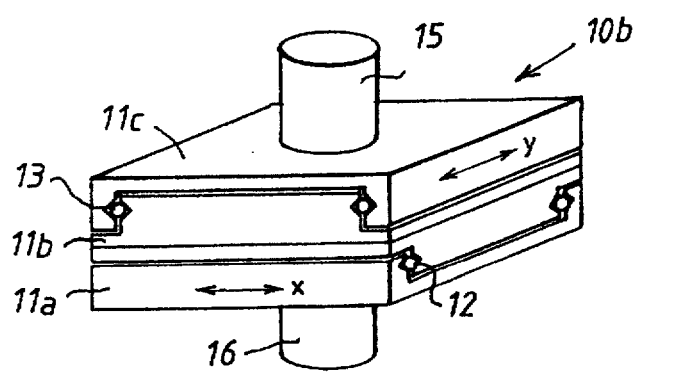
FIG. 2 is a perspective schematic representation of the motorized positioning device of the X-Y displacing device.

In FIG. 2, the motorized positioning unit 10b is shown as a component of the two-part X-Y displacing device 8. The motorized positioning unit 10b makes the defined positioning of the surgical microscope mounted thereon possible in a plane perpendicular to the axis A6. The positioning unit 10b is assembled from several individual parts (11a, 11b, 11c) which can be motor-displaced relative to each other. The individual parts (11a, 11b, 11c) are movable relative to each other via linear guides (12, 13). The motorized positioning unit 10b is mounted on the sensor unit 10a of the X-Y displacing device 8 via a connecting element 15. Below the motorized positioning unit 10b, the surgical microscope is attached to a connecting flange 16.

The configuration of the sensor unit 10a of the X-Y displacing device 8 is explained in more detail with respect to FIGS. 3 and 4 as is the first automated method step for balancing the stand, that is, for balancing the axis A6. In the embodiment shown in FIG. 1, the sensor unit 10a is mounted above the motorized positioning unit 10b and operates to detect the position of the gravity point of the load in the X-Y plane relative to the axis A6.

To obtain the desired balancing, the axis A6 is first positioned vertically which can be controlled by means of an inclination sensor in the X-Y displacing device. An inclinometer or even an electric spirit level can be utilized as a suitable inclination sensor. The perpendicular alignment of the axis A6 can be carried out manually by the visual control of the inclination sensor; however, it can likewise take place via a motorized control loop wherein the relative inclination is detected and a positioning of the axis A6 is achieved via a corresponding drive. The vertical alignment of the axis A6 is then achieved via the motorized displacement of the double articulated parallelogram about the axes A4 and A5. For this purpose, the corresponding brakes of these axes are released and the drives corresponding to these axes are driven via the respective control loops assigned to these axes.

After vertical alignment of the axis A6 is completed, the brakes corresponding to axes A4 and A5 are engaged. In the next step, the gravity point of the suspended load is brought into the extension of the vertically positioned axis A6. For this purpose, the torque applied by the load on the vertically positioned axis A6 is detected with the aid of the sensor unit 10a of the X-Y displacing device 8 and this torque is compensated via a control loop with the aid of a corresponding displacement of the suspended load by the positioning unit 10b.

Three force sensors are arranged radially symmetrically in an equilateral triangle in the sensor unit 10a of the X-Y displacing device 8 for detecting the torque acting on the axis A6. Alternatively, another arrangement of the force sensors is possible.

FIG. 3 shows a vertical section taken through the sensor unit 10a and only one of the force sensors 21a can be seen in this view. The force sensors 21a are mounted in a round can-shaped housing 20 and are attached via two screws (22a, 22b) to vertical ribs 28 of the can-shaped housing 20. The can-shaped housing 20 is connected via a connecting flange 23 to the interface of the vertical stand carrier arm and therefore to the axis A6. The actually acting load forces are introduced to the force sensors 21a via a central cylinder 24 mounted in the can-shaped housing 20. In this way, the torques acting on the axis A6 are detected. The cylinder 24 is threadably fastened to a connecting plate 25 which is connected to the force sensors 21a. In this way, force is introduced via the connecting plate to the force sensors 21a via two threaded pins (26a, 26b) which are lead from above and below to the force sensors 21a.

A ring-shaped leaf spring 27 is mounted between the force sensors 21a and the connecting plate 25. The leaf spring 27 is alternately connected to the connecting plate 25 and to the can-shaped housing 20. When a load is applied to the cylinder 24, the leaf spring 27 takes up displacements in the direction of the axis A6 and transmits these displacements to the force sensors 21a.

If a force acts on the cylinder 24, then each of the force sensors 21a is deflected by a specific measuring distance and registers an applied force. When forces are applied asymmetrically to the individual radially distributed force sensors 21a different forces are detected by the control unit connected thereto. A conclusion can be drawn as to the actual torque applied to the axis A6 from the known mounting geometry and a displacement of the suspended load is provided via the motorized positioning unit 10b until the actually detected torque is equal to zero. This is the case when all force sensors supply the same measuring signal, that is, the forces applied to the axis A6 are equally distributed in a rotational symmetrical manner.

The sensor unit 10a comprises a suspension part fixed to the stand and a load part movable for this purpose. The suspension part includes the can-shaped housing 20 and the load part includes the cylinder 24 and this assembly of the sensor 10a ensures that the torques acting on the axis A6 will be detected reliably when the resulting gravity point of the load does not yet lie in the extension of the perpendicularly positioned axis A6.

A developed schematic of the sensor unit 10a of FIG. 3 is shown in FIG. 4. The alternate attachment of the circular ring-shaped leaf spring 27 to the can-shaped housing 20 and the connecting plate 25 is clearly shown, that is, alternately to the load part and to the suspension part. In addition, FIG. 4 shows a second one of the three force sensors (21a, 21b) which is likewise connected via two threaded pins (26b, 27b) to the connecting plate 25 and therefore to the suspension part.

The described procedure for bringing the gravity point of the suspended load into the extension of the axis A6 is the same for both the open-loop control variation of the stand of the invention and for the closed-loop control variation thereof; that is, the first required control loop R1 is identical for both embodiments. The terms "open-loop control variation" and "closed-loop control variation" of the balanced stand are accordingly not to be understood that only the open-loop control or closed-loop control is to be utilized to achieve automatic balancing; instead, the so-called open-loop control variation also contains several closed-loop control circuits to provide a defined drive toward specific stand positions as well as the closed-loop control circuit R1 for the balancing of axis A6 just described.

The two automatic balancing methods differ only after the method step of balancing the axis A6.

Figure 5A:
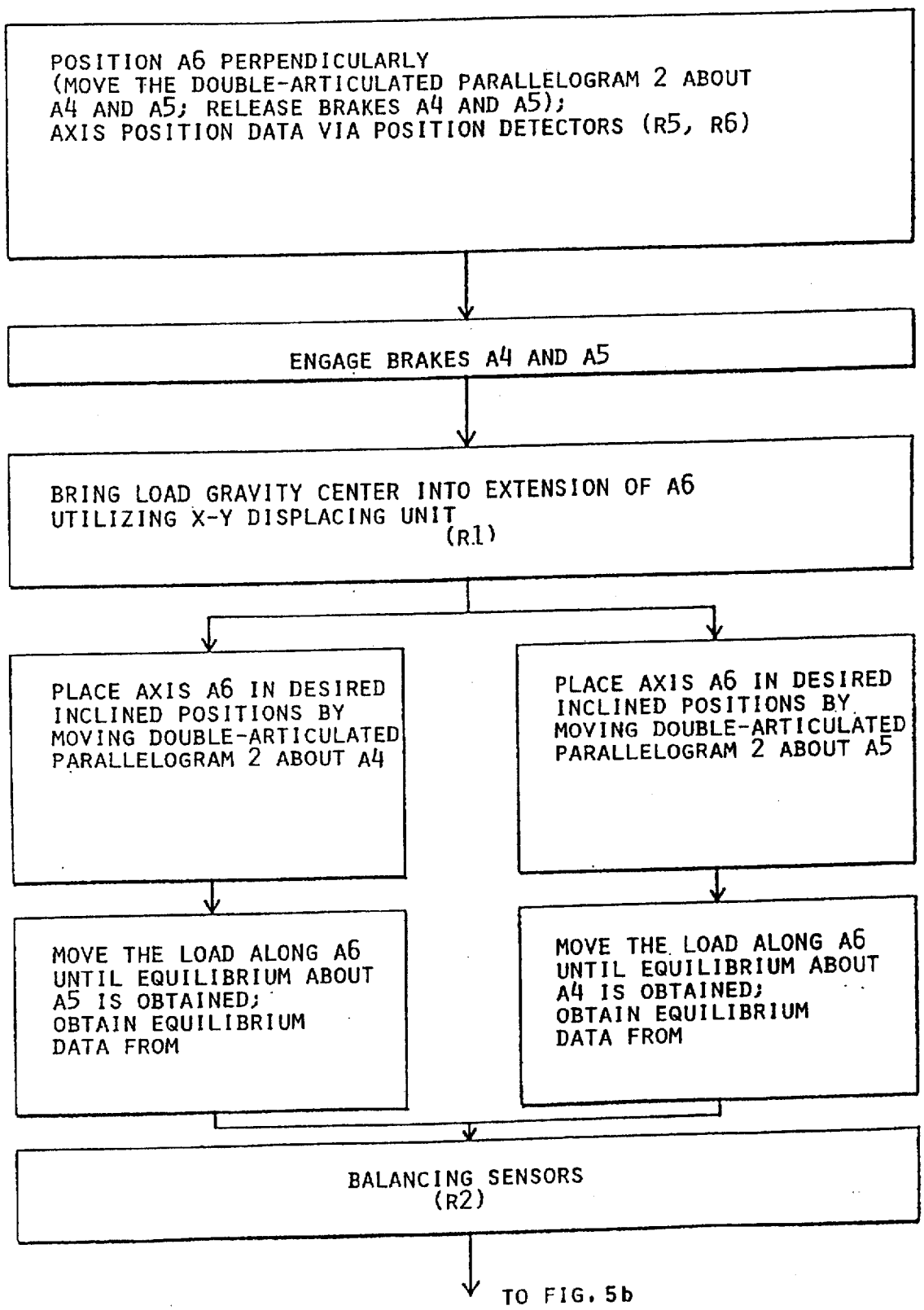

In the following, the automatic balancing procedure for the entire stand is first described which operates pursuant to the closed-loop control principle. A graphic representation of this sequence is provided in the flowchart of FIGS. 5a and 5b.

The method step described above is for automatically positioning the gravity point of the load in the extension of the vertically positioned axis A6 via the first control loop R1. After this method step, the axis A6 is sequentially inclined placed in desired positions about the axes A4 and A5 via motorized drives corresponding to these axes. The automatic balancing of the axis A6 about the two axes A4 and A5 takes place via the motorized displacement of the suspended load including the X-Y displacing device along the axis A6. For this purpose, the torque about the axes A4 or A5 is detected via suitable balancing sensors in a second closed-loop control circuit R2 and the load is motor-displaced correspondingly along the axis A6 until the desired balancing state is obtained. For the axis A4, a neutral balancing state is sought; whereas, a balancing state is realized for the axis A5 wherein the system gravity point lies on the axis A4.

The same torque caused by the load acts on the two axes A4 and A5 in the vertical direction. For this reason, one of the two balancing procedures can be omitted since this balancing is automatically guaranteed with the balancing of the other axis. Accordingly, a single second closed-loop control circuit loop R2 for balancing the axes A4 and A5 is required.

Thereafter, the automatic balancing of the articulated parallelogram 5 or the balancing of the axes A3 and A2 takes place. For this purpose, the articulated parallelogram 5 is first positioned vertically via the motorized drives of the axes A2 and/or A3. The detection of the actual position of the articulated parallelogram is achieved with the position detectors assigned to the axes A2 and/or A3. The closed-loop control circuits R7 and/or R8 effect the vertical alignment. In a third closed-loop control circuit R3, the torque about the axis A3 is detected by means of balancing sensors assigned to this axis and the compensating weight 6 is motor driven and functions as a torque compensating means. Thereafter, the articulated parallelogram is again arbitrarily positioned diagonally via the closed-loop control circuit R7 and/or R8 and the axis position data is detected via position detectors. A fourth closed-loop control circuit R4 ensures that a neutral equilibrium state is realized about the axis A2 by driving the compensating weight 7. For this purpose, the balancing sensors assigned to this axis continuously detect the actual balancing state. The entire stand is balanced after this method step.

Figure 6:
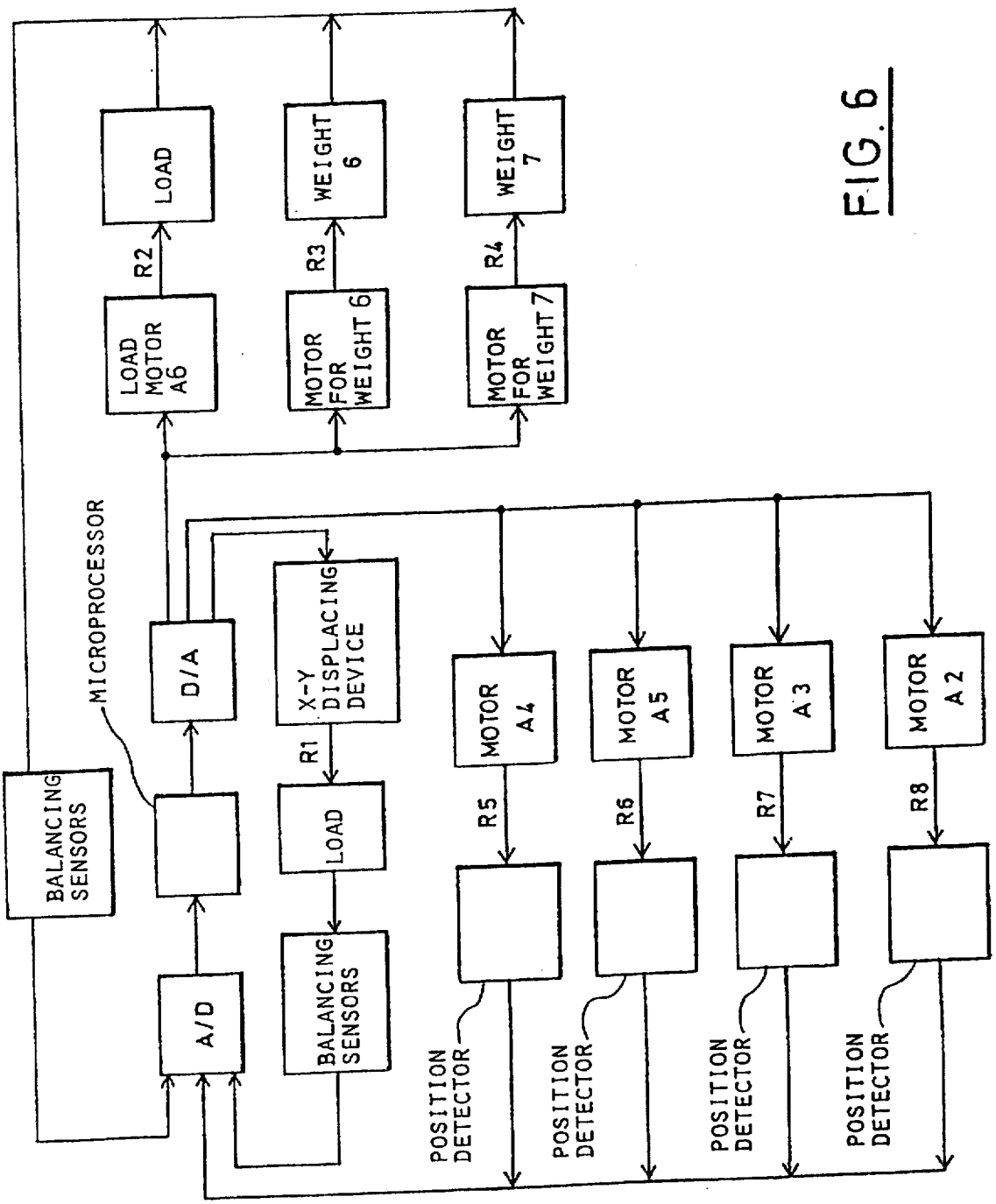
FIG. 6 is a block diagram for the signal processing showing the components necessary for this purpose in a stand which can be automatically balanced and which operates pursuant to the closed-loop control principle.

The signal paths including the required closed-loop control circuits for a completely automatically balanced stand are shown in a simplified form in FIG. 6 and operates according to the closed-loop control principle. Eight closed-loop control circuits R1 to R8 are provided for balancing the entire stand. These closed-loop control circuits are implemented by software, for example in a microprocessor of the connected control unit.

A first control loop R1 takes over the automatic balancing of the axis A6 with the aid of the X-Y displacing device. The second closed-loop control circuit R2 operates to balance the axis A5 and/or A4 via the translational movement of the load along the axis A6. A further closed-loop control circuit R3 is provided for balancing the axis A3 with the aid of the motor-displaceable weight 6. A fourth closed-loop control circuit R4 assumes the balancing of the axis A2 via the compensating weight 7. The respective unbalanced states of the four axes are detected via corresponding balancing sensors and transmitted via an A/D-converter to the microprocessor of the control unit. The control unit determines the required output variable in order to realize the desired balance state and transmits this output variable via a D/A-converter to the motor of the control loop which correspondingly drives the particular torque compensating means. This sequence is repeated for each of the closed-loop control circuits R1 to R4 until the desired balance state is achieved.

Four additional closed-loop control circuits R5 to R8 are required for the motorized drives of the axes A2 to A4 for the automatic balancing of the entire stand. The drives of the axes A2 to A5 automatically bring the stand into the positions required for equilibrium. The closed-loop control circuits R5 to R8 are likewise realized by the microprocessor of the control unit which drives these motors via its D/A-output, that is, via a corresponding D/A-converter. Position detectors detect the respective axis positions and have signals which are supplied via an A/D-converter to the microprocessor.

In an alternate embodiment of the stand of the invention, not all axes are balanced via separate closed-loop control circuits; instead, a partial balancing of individual axes takes place in accordance with the open-loop principle. In total, a lesser complexity with respect to apparatus and controls results in this embodiment than in the closed-loop control embodiment described above.

Figure 7A:
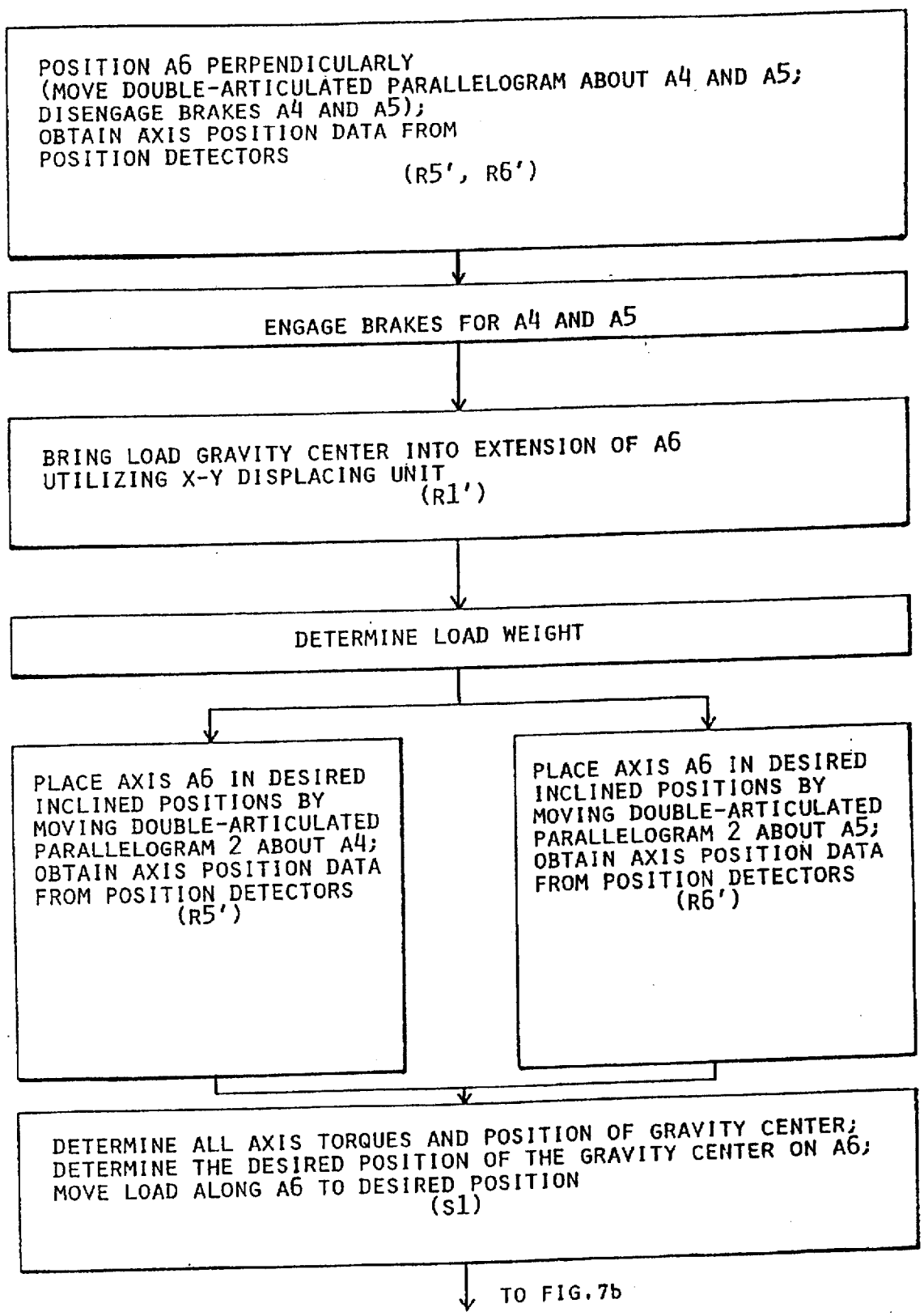
FIGS. 7a and 7b show a flowchart for the automated sequence of the balancing of the complete stand which operates pursuant to an open-loop control principle.
Figure 7B:
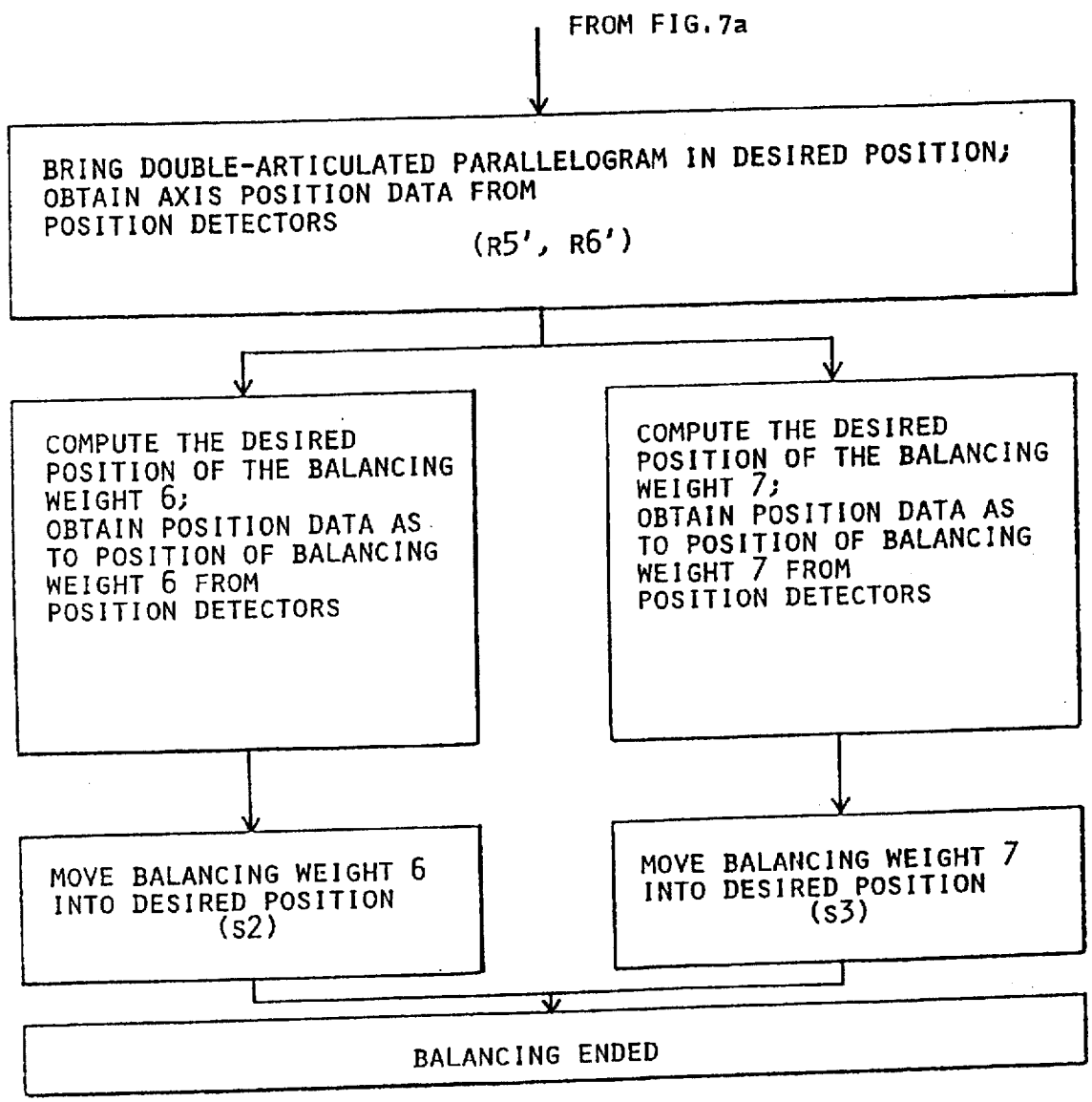

The individual method steps for automatically balancing this embodiment are explained with respect to the flowchart of FIGS 7a and 7b. The first method steps for balancing the axis A6 are identical to the method steps initially described for the closed-loop control embodiment of the stand of the invention. In the same manner, the axis A6 is positioned perpendicularly via the closed-loop control circuits R5' and R6', the brakes A4 and A5 are engaged and the load gravity center is driven into the extension of the axis A6 via the closed-loop control circuit R1' and the X-Y displacing device. Thereafter, the load weight is determined from the equilibrium measured values of the X-Y displacing device, that is, from the force sensors.

Thereafter, the axis A6 is placed in an inclined position about the axis A4 by a corresponding shift of the double articulated parallelogram via the closed-loop circuit R5'. At the same time, the amount of the particular shift is detected by means of position detectors. Alternatively, the same method can be carried out for the axis A5; that is, axis A6 can be placed in an inclined position about the axis A5 by a corresponding shift of the articulated parallelogram about axis A5. Here too, in each case, the selected axis position data is detected via position detectors.

From these detected measured values, that is, the detected the acting torques on axis A6 when shifting the axis A6 about A4 or about A5 for the known axis positions, the displacement $L_6$ of the load weight required for a neutral balance is computed by the microprocessor. For this purpose, all torques acting on the axis A6 as well as the position of the gravity center are determined from which, in turn, together with the known geometry of the stand, the desired gravity center position on axis A6 results. The load is thereafter motor-displaced by the specific displacement amount $L_6$ along axis A6. Thereupon, the articulated parallelogram is brought into any desired position via the closed-loop control circuits R5' and R6'. The axis position data can, if required, be detected via position detectors which, however, is not absolutely necessary.

In this method step, it is further not absolutely necessary that the double articulated parallelogram be motor driven into a defined position via the two closed-loop control circuits R5' and R6'; instead, for detecting measured values, a desired assumed position can be evaluated which reduces the complexity of the control.

Thereafter, the required desired positions of the compensating weights 6 and 7 are deduced from the determined torque values on the axis A6 for the known geometry of the stand. The compensating weights are then driven into the determined desired positions by the displacement amounts $L_2$ and $L_3$. The required displacement amounts again result from the known geometry of the stand.

The known stand geometry and the known torques acting on the respective axes can be evaluated for the required determination of the displacement amounts $L_6$, $L_2$ and $L_3$ in such a manner that, with respect to a comparison table implemented in the control unit, the detected measured values can be compared to empirically determined calibrating values. These calibrating values contain the required displacement data for defined stand positions and force relationships. The determined measured values are compared to these calibrated values and thereafter the load weight and the compensating weights are displaced by the corresponding displacement amounts. Such a comparison method can, for example, be realized with software via the connected control unit.

Figure 8:
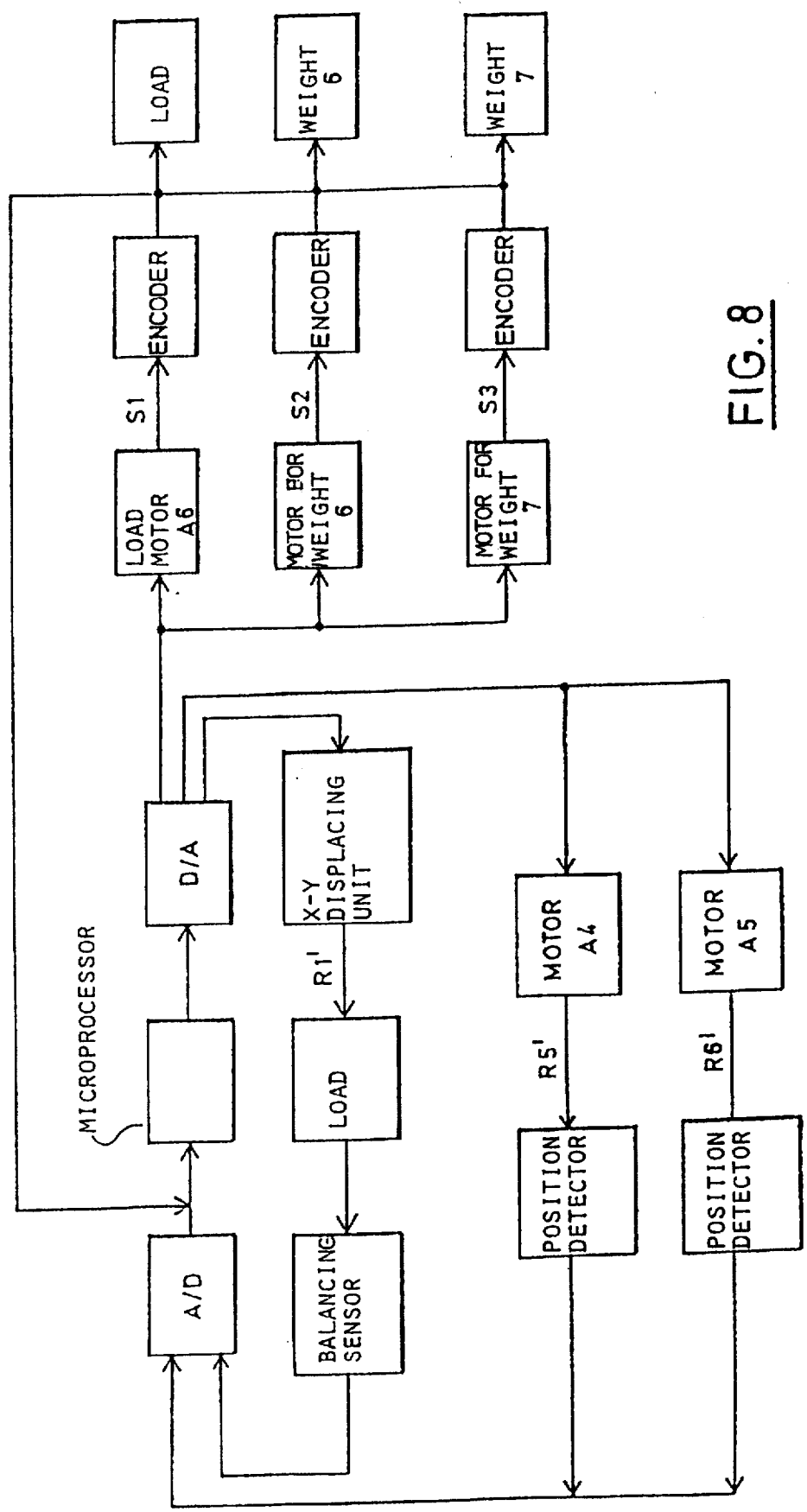
FIG. 8 is a block diagram showing the signal processing with the components required for this purpose in a stand which can be automatically balanced and which operates pursuant to an open-loop control principle; and, FIG. 9 is a perspective schematic diagram showing the assembly of another embodiment of the stand according to the invention including a control unit.

The signal paths of the embodiment of the stand of the invention which operates in accordance with the control principle described initially as well as the required open-loop circuits and closed-loop circuits are shown simplified in FIG. 8. For balancing the entire stand, three closed-loop control circuits R1', R5' and R6' as well as three open-loop control circuits S1 to S3 are provided in the open-loop embodiment already described. The open-loop control circuits and the closed-loop control circuits are built up in the same manner as in the embodiment, which is built-up completely in accordance with the closed-loop principle, via the microprocessor of the connected control unit. The first closed-loop control circuit R1' is identical to circuit R1' of the control variation described above. This first closed-loop control circuit R1' automatically balances the axis A6 with the aid of the X-Y displacing device. The axes A2 and A3 as well as A4 and A5 are balanced with the aid of the open-loop control circuits S1 to S3 which is in contrast to the closed-loop variation. The open-loop control circuit S1 assumes driving the load along the axis A6 by the specific displacement amount $L_6$. The actual load position on the axis A6 is detected by means of position detectors. The two other open-loop control circuits S2 and S3 provide a defined motorized displacement of the balancing weights 6 and 7 by the determined displacement amounts $L_1$ and $L_2$. The detection of the balancing weight positions on the articulated parallelogram 5 is likewise possible again by means of suitable position detectors.

The two closed-loop control circuits R5' and R6' are required in a fully automated embodiment in order to shift the balanced stand after balancing the axis A6 by means of closed-loop control circuit R1' about the axes A4 and A6 into respective desired positions. After the completed shifts about these two axes, the applied load torques or axis positions are detected and the required output variables for the three open-loop control circuits S1 to S3 are determined and transmitted to the corresponding open-loop control circuits. In principle, the required output variables can also be determined from desired positions of the parallelogram; that is, these closed-loop control circuits are not absolutely necessary for the defined displacement.

The microprocessor of the control unit detects in each case the actual position data or balancing data via an A/D-converter and determines the control variables of the three open-loop circuits S1 to S3. These control variables are outputted via a D/A-converter.

This variation of the balanced stand according to the invention permits a less complex dimensioning of the required open-loop or closed-loop control software.

A second embodiment of the stand of the invention including a suitable method for balancing the same is described with respect to FIG. 9.

The basic stand configuration comprising the vertical column 2 and the horizontal carrier arm 3 arranged so as to be movable with respect to the column corresponds substantially to the configuration of the first embodiment of FIG. 1. However, the horizontal carrier arm 3 is not configured as a double articulated parallelogram; instead, the carrier arm is alternately configured as a two-part carrier arm having compensating weights (8a, 8b, 9a, 9b). In addition, the X-Y displacing device 10 utilized in this embodiment does not include a sensor unit but only a positioning unit for transversely positioning a suspended load (not shown) relative to the axis A6.

The illustrated second embodiment of the stand of the invention comprises a vertical column 2 on which a horizontal, multi-part carrier arm 3 is articulately mounted. An interface 11 of the carrier arm is shown schematically and a load, such as a surgical microscope, can be mounted at the interface 11.

In the second embodiment, the vertical column 2 of the balanced stand includes a two-part configuration comprising a vertical stand base 12 and an articulated parallelogram 13 mounted so as to be movable relative to the stand base 12 about a horizontal axis A2. The upper part of the vertical stand base 12 is, in turn, movable about a vertical axis A1 relative to the lower part including the base part 1. For this purpose, an articulated element G1 is provided which is integrated into the vertical stand base 12. The articulated element G1 includes an actuable brake G1a and an angle encoder G1b.

Two motor-displaceable compensating weights (4, 5) are mounted on the articulated parallelogram 13 and are displaceable on threads in the direction of the arrows.

In a more complex embodiment of the stand of the invention, the actual positions of the compensating weights (4, 5) on the articulated parallelogram 13 can be detected by position detectors (not shown).

The articulated parallelogram 13 comprises several individual elements connected articulately to each other. The articulated parallelogram is itself movable about the axis A3 likewise orientated horizontally.

The horizontal carrier arm 3 is mounted at the upper end of the articulated parallelogram 13. The carrier arm 3 is, in turn, movable about its longitudinal axis, that is, the axis A4. The carrier arm 3 can be balanced about the axis A4 by means of displaceable balancing weights (8a, 8b, 9a, 9b). The interface part 14 of the carrier arm 3 is mounted at the forward end of the carrier arm so as to be movable about the axis A5. The interface part 14 of the carrier arm 14 is also movable about its longitudinal axis, that is, the axis A6. A further motor-driven compensating weight 15 is provided to balance about the axis A5.

The axes A1 to A6 of this embodiment of the automatically balanceable stand of the invention are assigned respective articulate elements G1 to G6 which include respective actuable brakes G1a to G6a as well as respective angle encoders G1b to G6b. The defined actuable brakes (G1a to G6a) can, for example, be configured as known electromotor brakes and make possible the defined blocking of the movement about an axis. The angle encoders G1b to G6b operate to detect the movement about an axis when this axis is not yet balanced and the angle encoders G1b to G6b are used in accordance with the invention as balancing sensors. Conventional incrementally or absolutely operating angle encoders can be used as suitable angle encoders and are available in a large selection from the Heidenhain Company of Germany.

Various compensating weights (4, 5, 8a, 8b, 9a, 9b, 15) are provided as torque compensating means in the embodiment shown in FIG. 9.

Positions of the stand can be detected by position detectors in a more complex embodiment in the stand of the invention. In the simple embodiment described, this is however not provided or is unnecessary.

The two compensating weights (4, 5) mounted on the articulated parallelogram operate for balancing the articulated parallelogram about the axes A2 and A3 and can be displaced by a electric motors on windings in the direction of the arrows.

Other embodiments are possible as an alternative to displacing the compensating weights via windings.

Displaceable compensating weights (8a, 8b, 9a, 9b) are provided for balancing the carrier arm 3 about the axis A4 in the direction of the arrows.

A further motor-displaceable compensating weight 15 operates for balancing about axis A5.

A control unit 16 is required for automatically balancing this embodiment of the stand of the invention. The control unit 16 is realized in the embodiment of FIG. 9 with software via a computer having an input interface 6 and a display 7. Via the display 7, the interactive balancing by a user is possible in such a manner that the user continuously receives instructions as to the required method steps.

The method sequence for automatic balancing of the embodiment of the stand of the invention of FIG. 9 is described in the following. First, the completely unbalanced stand is brought by the user into a balance base position which corresponds approximately to the position shown in FIG. 9. For this purpose, the control unit 16 switches all actuable brakes G1a to G6a on the stand advantageously to a reduced holding torque. After the balance base position is assumed, all brakes are again positioned to a full holding torque.

In the first method step, the stand of the invention or the stand base 1 is horizontally aligned, for example, with the aid of a spirit level in the stand base. This method step is only necessary when the axis A1 is intended to be balanced and can be dropped as may be required.

In the next method step, axis A6 is balanced by moving the X-Y displacing device 10. For this purpose, the control unit 16 briefly releases the brake G6a assigned to the axis A6 for a defined time duration T. The corresponding encoder G6b of the joint G6 determines the movement which has taken place relative to the axis A6. The detected rotational angle and the time duration T of the release of the brake G6a are further processed by the control unit 16 in such a manner that the required amount is determined by which the X-Y displacing device must be moved. This amount can be determined, for example, via a stored reference table having various possible parameter combinations of rotational angles and time durations T and can be transmitted via an open-loop control circuit to the X-Y displacing device.

Alternatively, the X-Y displacing device 10 can be driven by the required amount via a closed-loop control circuit.

This method step is then iteratively repeated until the rotation angle sensor G6b no longer registers movement relative to the axis A6.

Thereafter, the user rotates the axis A6 by approximately 45° whereafter the corresponding brakes are again set to the reduced holding torque.

The foregoing can also take place automatically via the control unit 16 in a more complex embodiment having drives assigned to the axes. Thereafter, and as in the method step described above, balancing about the axis A6 takes place. After this step, the two main inertia axes of the axis A6 are balanced.

The axis A5 is automatically balanced in the next method step. The control unit 16 again initiates a short-term release of the brake G5a assigned to this axis for a defined time duration T. The corresponding angle encoder G5b detects the movement, which has taken place because of the unbalanced mass relative to the axis A5 and transmits this value to the control unit 16. The control unit 16 then again computes the travel distance for the balancing weight 15 on the basis of the time duration T and the measured rotational angle relative to the axis A5. The compensating weight 15 is correspondingly driven 30 and displaced. This method can be carried out iteratively until a balanced state is present about axis A5.

In the following method step, the axis A4 is balanced in the same manner as in the two previously described method steps. This means that after detecting the unbalanced state via the angle sensor G4b of the rotational joint G4, the balancing weights (8a, 8b, 9a, 9b) are correspondingly driven via open-loop control circuits or closed-loop control circuits until no rotation about this axis takes place any longer. As with the balancing procedure about the axis A6, the axis A4 is balanced in at least two positions separated by 45°.

In the next method step, the axis A3 is balanced with the balancing weight 4 being driven correspondingly on the articulated parallelogram. The same method takes place in accordance with this balancing step for the axis A2 by correspondingly displacing the other balancing weight 5 on the articulated parallelogram.

The entire stand is now completely automatically balanced and a final total test can take place via the control unit 16. For this purpose, each brake is disengaged for a short time and it is registered as to whether the particular angle encoder determines a movement. If this is the case, then appropriate action by the torque compensating means assigned to this axis is required.

The stand is now completely balanced and can be utilized in the usual manner.

As already indicated several times above, the stand of the invention can be equipped with drives for the individual axes so that the complete balancing procedure is possible without manual action of the operating personnel. In addition, the balancing weights acting as torque compensating means can be provided with position detectors which make possible a precise detection of the actual positions.

In addition, it is possible that not all axes but only a series of desired axes are balanced in the manner described.

It is understood that the foregoing description is that of the preferred embodiments of the invention and that various changes and modifications may be made thereto without departing from the spirit and scope of the invention as defined in the appended claims.

What is claimed is:

1. A stand for mounting a diagnostic and/or therapeutic device defining a load, the stand comprising:
   a base;
   a plurality of interconnected elements mounted on said base and defining at least one axis about which said elements are movable relative to said base;
   a balancing sensor assigned to said axis for detecting an unbalanced state relative to said axis and for supplying a sensor output signal indicative of said unbalanced state;
   a motor-driven torque compensator for acting on said axis; and,
   a balancing control circuit for acting on said motor-driven torque compensator in response to said sensor output signal until a state of equilibrium is obtained about said axis.

2. The stand of claim 1 said balancing control circuit being an open-loop control circuit.

3. The stand of claim 1, said balancing control circuit being a closed-loop control circuit.

4. The stand of claim 1, further comprising an X-Y displacing device arranged between said stand and a load for displacing said load in the X-Y plane defining a X-direction and a Y-direction, the 2 X-Y displacing device including:
   a motor for positioning said load in said X-Y plane;
   an additional balancing sensor for detecting the load forces applied to said X-Y displacing device in at least one of said X-direction and said Y-direction; and,
   an additional balancing control circuit for acting on said motor in response to the output of said additional balancing sensor until said load is balanced in said X-Y plane.

5. A stand for mounting a diagnostic and/or therapeutic device defining a load, the stand comprising:
   a base;
   a plurality of interconnected elements mounted on said base and defining a plurality of axes about which said elements are movable relative to said base;
   a plurality of balancing sensors assigned to corresponding ones of said axes for detecting respective unbalanced states relative to said axes, respectively, and for supplying corresponding sensor output signals indicative of said unbalanced states, respectively;
   a plurality of motor-driven torque compensators for acting on corresponding ones of said axes;
   a plurality of balancing control circuits for acting on corresponding one of said motor-driven torque compensators in response to said sensor output signals, respectively, until corresponding states of equilibrium are obtained about said axes, respectively.

6. The stand of claim 5, said plurality of control circuits including open-loop and/or closed-loop control circuits.

7. The stand of claim 6, said balancing sensors being provided for detecting static forces.

8. The stand of claim 6, said balancing sensors being provided for detecting relative inclinations.

9. The stand of claim 6, said balancing sensors being provided for detecting torques.

10. The stand of claim 6, each of said balancing sensors being an angle encoder for detecting relative movements of the axis corresponding thereto in the unbalanced state.

11. The stand of claim 10, said angle encoders supplying rotational angle measured values; and, further comprising a control unit for determining stereotactical coordinates from said rotational angle measured values.

12. The stand of claim 6, at least one of said motor-driven torque compensators being a motor-displaceable compensating weight displaceable relative to the axes of said stand and said stand further comprising at least one position detector for detecting the position of said compensating weight.

13. The stand of claim 6, at least one of said motor-driven torque compensators being a motor-displaceable spring for providing a defined setting of compensating torque; and, torque detecting means for detecting said compensating torque.

14. The stand of claim 6, one of said interconnected elements being a vertical column and a first predetermined number of other ones of said interconnected elements conjointly defining a horizontal carrier arm; and, said carrier arm defining an interface for attaching said load.

15. The stand of claim 14, said one element including a vertical base; and, a second predetermined number of other ones of said interconnected elements conjointly defining an articulated parallelogram pivotally mounted on said vertical base so as to be movable about a horizontal axis.

16. The stand of claim 14, said first predetermined number of other ones of said interconnected elements conjointly defining a double-articulated parallelogram.

17. The stand of claim 6, further comprising a microprocessor for implementing said open-loop and/or closed-loop control circuits.

18. The stand of claim 6, further comprising an electromechanical brake assigned to at least one of said axes; and, a control unit for actuating said electromechanical brake.

19. The stand of claim 18, said control unit defining at least one of said control circuits for balancing one of said axes; said control circuit being adapted to process the time span T during which said electromechanical brake is released and the rotational movement about said one axis during said time span as a balancing actuating variable and to then determine a control variable for actuating the torque compensator corresponding to said one axis and for correspondingly driving said torque compensator.

20. The stand of claim 19, said torque compensator comprising a motor-displaceable balancing weight.

21. The stand of claim 19, said control unit including a display containing balancing instructions for the user.

22. The stand of claim 6, a plurality of electromechanical brakes assigned to corresponding ones of said axes and a control unit for actuating said electromechanical brakes; said control unit defining said control circuits for balancing said axes, respectively; said control unit being adapted to process a respective time spans T during which said electromechanical brakes are released and the rotational movements about the axes as balancing actuating variables and to then determine control variables for actuating the respective torque compensators corresponding to the respective axes and for correspondingly driving said torque compensators; each of said torque compensators including a motor-displaceable balancing weight and a position detector for detecting the position of the balancing weight.

23. The stand of claim 6, one of said various loads being a surgical microscope.

24. An X-Y displacing device for a stand for mounting a diagnostic and/or therapeutic device defining a load, the stand including a base, a plurality of interconnected elements mounted on said base and defining one or more axes about which the elements are movable relative to said base, the X-Y displacing device being arranged between the stand and said load for displacing said load in the X-Y plane defining a X-direction and a Y-direction, the X-Y displacing device comprising:

a motor for positioning said load in said X-Y plane;

at least one balancing sensor for detecting the load forces applied to said X-Y displacing device in at least one of said X-direction and said Y-direction; and, a balancing control circuit for acting on said motor in response to the output of said sensor until said load is balanced in said X-Y plane.

25. The X-Y displacing device of claim 24, further comprising an inclination sensor.

26. The X-Y displacing device of claim 24, further comprising three of said balancing sensors for detecting said applied load forces and said three balancing sensors being arranged radially symmetrically in said device; and, means for movably connecting said three sensors to said stand and to said one load so as to permit said three sensors to move over a defined measurement path.

27. A method of balancing a stand for mounting a diagnostic and/or therapeutic device defining a load wherein the balancing is at least partially automated, the stand including a base, a plurality of interconnected elements mounted on said base and defining one or more axes about which the elements are movable relative to said base, the method comprising the steps of:

detecting an unbalanced state of at least one of said axes utilizing a balancing sensor; and, providing a closed-loop balancing control circuit for at least one of said axes for acting on a motor-driven torque compensator until said axis reaches a state of equilibrium.

28. The method claim 27, the stand being movable about a plurality of axes and the method further comprising:

providing a separate closed-loop control circuit for each of said axes to be balanced; and, sequentially balancing all of said axes to be balanced.

29. A method of balancing a stand for mounting a diagnostic and/or therapeutic device defining a load wherein the balancing is at least partially automated, the stand including a base, a plurality of interconnected elements mounted on said base and defining one or more axes about which the elements are movable relative to said base, the method comprising the steps of:

detecting an unbalanced state of at least one of said axes utilizing a balancing sensor;

determining a required actuating variable for a motor-driven torque compensator; and, providing an open-loop control circuit for at least one of said axes and allowing said actuating variable to act on said motor-driven torque compensator for said one axis.

30. The method of claim 29, further comprising the step of:

providing a plurality of said open-loop control circuits separately for all of said axes which are to be balanced; and, sequentially balancing all of said axes.

31. The method of claim 29, further comprising the steps of:

providing a plurality of said balancing sensors as angle encoders for corresponding ones of said axes for detecting the resulting rotational movements, respectively, in the unbalanced state of said axes within a defined time T; and, utilizing the detected movements as actuating variable for a plurality of motor-driven torque compensators within a plurality of open-loop and/or closed-loop control circuits, respectively, so as to cause said torque compensating means to act on said axes, respectively, until respective equilibrium states are reached relative to said axes, respectively.

32. The method of claim 31, further comprising:

after completing the method steps, conducting a concluding overall test which includes the steps of releasing respective brakes assigned to said axes for a short time interval and registering any additional rotational movements which may occur; and, balancing those ones of said axes with respect to which an additional rotational movement has occurred.

* * * * *

UNITED STATES PATENT AND TRADEMARK OFFICE
CERTIFICATE OF CORRECTION

PATENT NO. : 5,667,186
DATED : September 16, 1997
INVENTOR(S) : Joachim Luber, Martin Pelzer, Heinz Jakubowski, Arvids Mackevics, Annette Reiss and Juergen Schweizer It is certified that error appears in the above-identified patent and that said Letters Patent is hereby corrected as shown below:

In column 6, line 32: between "21a" and "different", insert -- , --.

In column 8, line 37: delete "FIGS" and substitute -- FIGS. -- therefor.

In column 12, line 35: delete "30".

In column 13, line 29, delete "1" and substitute -- 1, -- therefor.

In column 13, line 35: delete "the" and substitute -- a -- therefor.

In column 13, line 36: delete "2".

UNITED STATES PATENT AND TRADEMARK OFFICE
CERTIFICATE OF CORRECTION

PATENT NO. : 5,667,186
DATED : September 16, 1997
INVENTOR(S) : Joachim Luber, et al.

It is certified that error appears in the above-identified patent and that said Letters Patent is hereby corrected as shown below:

In column 13, line 60: delete "one" and substitute -- ones -- therefor.

In column 14, line 43: delete "the" and substitute -- a -- therefor.

Signed and Sealed this

Seventh Day of April, 1998

Attest:

BRUCE LEHMAN

Attesting Officer      Commissioner of Patents and Trademarks